US006291471B1

(12) United States Patent
Kling et al.

(10) Patent No.: US 6,291,471 B1
(45) Date of Patent: *Sep. 18, 2001

(54) USE OF APOMORPHINE FOR THE TREATMENT OF ORGANIC ERECTILE DYSFUNCTION IN MALES

(75) Inventors: Karen Kling, Libertyville; Renee J. Perdok, Gurnee; Dustin D. Ruff, Grayslake, all of IL (US)

(73) Assignee: ABB Holdings, Inc., Lake Forest, IL (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/213,567

(22) Filed: Dec. 17, 1998

(51) Int. Cl.$^7$ .................................................. A61K 31/44
(52) U.S. Cl. ............................................................ 514/284
(58) Field of Search ............................................. 514/284

(56) References Cited

U.S. PATENT DOCUMENTS

| 5,256,652 | 10/1993 | El-Rashidy et al. ................. 514/58 |
|---|---|---|
| 5,270,323 | 12/1993 | Milne, Jr. et al. .................. 514/309 |
| 5,292,520 | 3/1994 | de Haan et al. ..................... 424/465 |
| 5,441,747 | 8/1995 | de Haan et al. ..................... 424/465 |
| 5,562,917 | 10/1996 | Durif et al. ........................... 424/447 |
| 5,624,677 | * 4/1997 | El-Rashidy et al. ................ 424/435 |
| 5,688,499 | 11/1997 | Banting et al. . |
| 5,756,483 | 5/1998 | Merkus ................................. 514/58 |
| 5,770,606 | * 6/1998 | El-Rashidy et al. ................ 514/284 |
| 5,888,534 | 3/1999 | El-Rashidy et al. ................ 424/435 |

FOREIGN PATENT DOCUMENTS

| WO 97/33608 | 9/1997 | (WO) . |
|---|---|---|
| WO 98/26763 | 6/1998 | (WO) ............................. A61K/9/20 |
| WO 98/48781 | 11/1998 | (WO) ............................. A61K/9/22 |

OTHER PUBLICATIONS

Lue, T. F. "Impotence: a patient's goal–directed approach to treatment." *World Journal of Urology*, vol. 8, 1990, pp. 67–74.

NIH Consensus Development Panel on Impotence, "Impotence." *The Journal of the American Medical Association*, vol. 270(1), Jul. 1993, pp. 83–90.

Feldman, H. A., et al. "Impotence and its Medical and Psychosocial Correlates: Results of the Massachusetts Male Aging Study." *The Journal of Urology*, vol. 151, Jan. 1994, pp. 54–61.

Sachs, B. D., et al. "Effects of Copulation on Apomorphine–Induced Erection in Rats." *Pharmacology Biochemistry and Behavior*, vol. 48(2), 1994, pp. 423–428.

Heaton, J. P. W., et al., "Recovery of Erectile Function by the Oral Administration of Apomorphine." *Urology*, vol. 45(2), Feb. 1995, pp. 200–206.

Levine, L. A., et al. "Use of Nocturnal Penile Tumescence and Rigidity in the Evaluation of Male Erectile Dysfunction." *Urologic Clinics of North America*, vol. 22(4), Nov. 1995, pp. 775–788.

Meuleman, E. J., et al., "Investigation of Erectile Dysfunction." *Urologic Clinics of North America*, vol. 22(4), Nov. 1995, pp. 803–819.

O'Leary, M. P., et al. "A Brief Male Sexual Function Inventory for Urology." *Urology*, vol. 46(5), 1995, pp. 697–706.

Boolell, M., et al., "Sildenafil, a novel effective oral therapy for male erectile dysfunction." *British Journal of Urology*, vol. 78, Apr. 1996, pp. 257–261.

Linet, O. I., et al. "Efficacy and Safety of Intracavernosal Alprostadil in Men With Erectile Dysfunction." *The New England Journal of Medicine*, vol. 334, Apr. 1996, pp. 873–877.

Jarow, J. P., et al. "Outcome Analysis of Goal Directed Therapy For Impotance." *The Journal of Urology*, vol. 155, May 1996, pp. 1609–1612.

Muller, J. E., et al. "Triggering Myocardial Infarction by Sexual Activity." *JAMA*, vol. 275(18), May 1996, pp. 1405–1409.

Montague, D. K., et al. "Clinical Guidelines Panel on Erectile Dysfunction: Summary Report on the Treatment of Organic Erectile Dysfunction." *The Journal of Urology*, vol. 156, Dec. 1996, pp. 2007–2011.

Padma–Nathan, H. et al. "Treatment of Men With Erectile Dysfunction With Transurethral Alprostadil." *The New England Journal of Medicine*, vol. 336(1), Jan. 1997, pp. 1–7.

Heaton, J. P. W., et al. "A therapeutic taxonomy of treatments for erectile dysfunction: an evolutionary imperative." *International Journal of Impotence Research*, vol. 9, 1997, pp. 115–121.

Rosen, R. C., et al. "The International Index of Erectile Function (IIEF): A Multidimensional Scale For Assessment of Erectile Dysfunction." *Urology*, vol. 49(6), 1997, pp. 822–830.

Cutler, S. J., et al. "Treatment of Sexual Dysfunction." *U.S. Pharmacist*, May 1998, (downloaded from the internet at http://www.uspharmacist.com/issues/1998/may/sex.htm) 10 sheets.

"Cardiovascular Disease, Sexual Activity and Impotence." *ESIR* newsletter #4, Aug. 1998, (downloaded from the internet at http://esir.com/newsletter/ago98/5.htm) 2 sheets.

(List continued on next page.)

Primary Examiner—Russell Travers
(74) Attorney, Agent, or Firm—James D. McNeil

(57) ABSTRACT

A method of treating organic erectile dysfunction, particularly vasculogenic erectile dysfunction comprises administering to a male in need of such treatment a therapeutically effective amount of apomorphine or a pharmaceutically acceptable salt or pro-drug thereof.

21 Claims, No Drawings-

OTHER PUBLICATIONS

Coleman, E. *Sexual Health Today*, vol. 1(4), 1998, (downloaded from the internet at http://www.med.umn.edu/fp/phs/sht/shtv1n04.htm) 8 sheets.

Heaton, J. P. W. "Neural and pharmacological determinants of erection." *International Journal of Impotence Research*, vol. 10(Suppl. 2), 1998, pp. S34–S39.

TLC Pharmacy Men's Newsletter, "Oral Medications for Impotence." Issue 2, (downloaded from the internet at http://www.tlcpharmacy.com/mends_newsletter_2.html) Date unknown.3 sheets. (Nov. 15, 1998).

DiPiro et al., Pharmacotherapy: A Pathophysiologic Approach, New York: Elsevier, pp. 456–467, 1989.*

* cited by examiner

USE OF APOMORPHINE FOR THE TREATMENT OF ORGANIC ERECTILE DYSFUNCTION IN MALES

TECHNICAL FIELD

This invention relates to medical methods of treatment. More particularly, the invention concerns the use of apomorphine for the treatment of organic erectile dysfunction in males, particularly vasculogenic erectile dysfunction.

BACKGROUND OF THE INVENTION

In the medical literature the less precise term, "impotence" has been replaced by the term "erectile dysfunction." This term has been defined by the National Institutes of Health as the inability of the male to attain and maintain erection of the penis sufficient to permit satisfactory sexual intercourse. J. Am. Med. Assoc., 270(1):83–90 (1993). Because adequate arterial blood supply is critical for erection, any disorder that impairs blood flow may be implicated in the etiology of erectile failure. Erectile dysfunction affects millions of men and, although generally regarded as a benign disorder, has a profound impact on their quality of life. It is recognized, however, that in many men psychological desire, orgasmic capacity, and ejaculatory capacity are intact even in the presence of erectile dysfunction.

Etiological factors for erectile disorders have been categorized as psychogenic or organic in origin. Organic factors include those of a neurogenic origin and those of a vasculogenic origin. Neurogenic factors include, for example, lesions of the somatic nervous pathways which may impair reflexogenic erections and interrupt tactile sensations needed to maintain erections, and spinal cord lesions which, depending upon their location and severity, may produce varying degrees of erectile failure.

Psychogenic factors for erectile dysfunction include such processes as depression, anxiety, and relationship problems which can impair erectile functioning by reducing erotic focus or otherwise reducing awareness of sensory experience. This may lead to an inability to initiate or maintain an erection.

Vasculogenic risk factors include factors which affect blood flow and include cigarette smoking, diabetes mellitus, hypertension, vascular disease, high levels of serum cholesterol, low levels of high-density lipoprotein (HDL), and other chronic disease conditions such as arthritis. The Massachusetts Male Aging Study (MMAS, as reported by H. A. Feldman, et al., J. Urol., 151: 54–61 (1994) found, for example, that the age-adjusted probability of complete erectile dysfunction was three times greater in subjects reporting treated diabetes than in those without diabetes. While there is some disagreement as to which of the many aspects of diabetes is the direct cause of erectile dysfunction, vascular disease is most frequently cited.

The MMAS also found a significant correlation between erectile dysfunction and heart disease with two of its associated risk factors, hypertension and low serum high density lipoprotein (HDL). It has been reported that 8–10% of all untreated hypertensive patients are impotent at the time they are diagnosed with hypertension. The association of erectile dysfunction with vascular disease in the literature is strong, with impairments in the hemodynamics of erection demonstrated in patients with myocardial infarction, coronary bypass surgery, cerebrovascular accidents, and peripheral vascular disease. The MMAS also found cigarette smoking to be an independent risk factor for vasculogenic erectile dysfunction, with cigarette smoking found to exacerbate the risk of erectile dysfunction associated with cardiovascular diseases.

The treatment of erectile dysfunction varies, depending upon the root causes of the condition in a particular patient. The mode of treatment may involve the use psychotherapeutic, surgical, mechanical, or pharmacotherapeutic methodology. Psychotherapy and/or behavioral therapy are often useful for some patients with erectile dysfunction with no obvious organic cause (psychogenic). Venous ligation is effective in the treatment of patients who have difficulty maintaining an erection due to demonstrated venous leakage from the *corpus cavernosa*. Vacuum constriction devices are sometimes effective in generating and maintaining erections in patients with erectile dysfunction, and semi-rigid, malleable, or inflatable penile prostheses are available for patients who fail or refuse other forms of therapy.

Pharmacologic agents which have been used in the treatment of erectile dysfunction include vasodilators which are injected directly into the body of the penis, as well as orally administered agents. The most effective and well-studied of the injectable vasodilators are papaverine hydrochloride, phentolamine, and alprostadil, used singly or in combination. However, use of penile vasodilators can be problematic in patients who cannot tolerate transient hypotension. Orally administered agents include yohimbine, bromocriptine, fluoxetine, trazadone, trental, sildenafil, phentolamine, and extracts of *ginkgoacea biloba*.

U.S. Pat. No. 5,770,606 discloses the sub-lingual administration of apomorphine for the treatment of psychogenic erectile dysfunction in males. Apomorphine, a derivative of morphine, was first evaluated for use as a pharmacologic agent as an emetic in 1869. In the first half of the $20^{th}$ century, apomorphine was used as a sedative for psychiatric disturbances and as a behavior-altering agent for alcoholics and addicts. By 1967, the dopaminergic effects of apomorphine were realized, and the compound underwent intensive evaluation for the treatment of Parkinsonism. Since that time, apomorphine has been classified as a selective dopamine receptor agonist that stimulates the central nervous system producing an arousal response manifested by yawning and penile erection in animals and man.

SUMMARY OF THE INVENTION

It has been found, in accordance with the present invention that organic erectile dysfunction in a male can be effectively treated or ameliorated by administering to a male in need of such treatment a therapeutically effective amount of apomorphine or a pharmaceutically acceptable salt, ester, or pro-drug thereof. In particular, organic erectile dysfunction having a vasculogenic origin is effectively treated by oral administration of apomorphine.

In accordance with the invention, apomorphine is administered in an amount sufficient to produce an effective penile erection, but insufficient to induce nausea, typically in doses which result in an amount sufficient to establish plasma concentration levels of apomorphine preferably ranging up to about 5.5 nanograms/mL. The compound or one of its appropriate salts or pro-drugs may be administered alone or, if needed at the higher end of the dose range, in combination with an anti-emetic agent.

DETAILED DESCRIPTION

As used throughout this specification and the appended claims, the term "vasculogenic erectile dysfunction" refers to the condition whereby a male is incapable of initiating and/or maintaining a penile erection sufficient for satisfactory intercourse due to diminished blood flow accompanying a disease of the cardiovascular system and/or an associated risk factor. Such diseases include, but are not limited to, myocardial infarction, heart disease, peripheral vascular disease, and impaired circulation resulting from diabetes, cigarette smoking, cardiac bypass surgery, and cerebrovascular accidents. Associated risk factors include hypertension, elevated serum low-density lipoprotein (LDL) and low serum high density lipoprotein (HDL).

The terms "acute dose" or "acute administration" mean the scheduled administration of a drug to the patient on an as-needed basis.

The term "co-administration" of two or more pharmacologic agents means the administration of the two or more agents together in a single unit dosage form or, alternatively, in two or more separate unit dosage forms, one immediately following the other.

The terms "effective vasocongestive arousal" or "effective erection" mean, the swelling or tumescence of the male penis sufficient to effect vaginal penetration.

The method of treatment of the present invention involves the administration of apomorphine or one of its pharmaceutically acceptable acid addition salts, pro-drug or pro-drug ester to a patient suffering vasculogenic erectile dysfunction. Apomorphine, (R)-5,6,6a,7-tetrahydro-6-methyl-(4H-dibenzo[de,g]quinoline-10,11-diol, is a derivative of morphine obtained by treatment of the latter with concentrated hydrochloric acid (L. Small, et al., *J. Org. Chem.*, 5: 334 (1940)) or by heating morphine with zinc chloride (Mayer, *Ber.*, 4: 171 (1871)). The compound has the chemical structure:

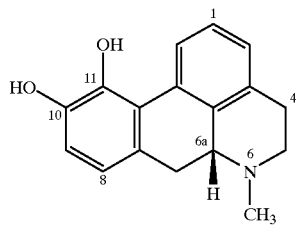

Apomorphine and possesses a chiral center at position 6a. The total synthesis of the racemic mixture is reported by J. L. Neumeyer, et al., *J. Pharm. Sci.*, 59:1850 (1970) and the synthesis of the separate enantiomers by V. J. Ram and J. L. Neumeyer, *J. Org. Chem.*, 46: 2830 (1981). The compound possesses a basic nitrogen atom at position 6 and is thus capable of existing in the free base form as well as acid addition salt forms.

The compound may be administered as the free base or in the form of one of its more soluble pharmaceutically acceptable salts or pro-drug derivatives. Administration of the racermic form, or either of the enantionmers, alone, or in various combinations, is contemplated as falling within the scope of this invention.

As used herein, the term "pharmaceutically acceptable salt" refers to those salts which are within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge, et al. describe pharmaceutically acceptable salts in detail in *J. Pharmaceutical Sciences*, 66: 1–19 (1977). The salts are prepared in situ during the final isolation and purification of the compounds of the invention, or separately by reacting the free base function with a suitable organic acid. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like.

The term "pro-drug" refers to compounds that are rapidly transformed in vivo to yield the parent compound, as for example, by hydrolysis in blood. T. Higuchi and V. Stella provide a thorough discussion of the pro-drug concept in "Pro-drugs as Novel Delivery Systems", Vol. 14 of the A.C.S. Symposium Series, American Chemical Society (1975). Examples of esters useful as pro-drugs for compounds containing carboxyl groups may be found on pages 14–21 of "Bioreversible Carriers in Drug Design: Theory and Application," edited by E. B. Roche, Pergamon Press (1987).

The term "pro-drug ester group" refers to any of several ester-forming groups that are hydrolyzed under physiological conditions. Examples of pro-drug ester groups include pivoyloxymethyl, acetoxymethyl, phthalidyl, indanyl and methoxymethyl, as well as other such groups known in the art.

As used herein, the term "pharmaceutically acceptable ester" of apomorphine refers to esters formed with one or both of the hydroxyl functions at positions 10 and 11, and which hydrolyze in vivo and include those that break down readily in the human body to leave the parent compound or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl moiety advantageously has not more than 6 carbon atoms. Examples of particular esters includes formates, acetates, propionates, butyrates, acrylates and ethylsuccinates.

For an optimal vasocongestive arousal response (erection) in the male, steady state circulating serum and mid-brain tissue levels of apomorphine should be maintained within a relatively closely defined range. The drug is preferably administered in a formulation which rapidly delivers the drug to the system while maintaining and not exceeding the desired systemic levels of the drug. Methods known to the practitioner of the pharmaceutical formulation arts which accomplishes this means may be used. For example, the drug may be delivered to the system by means of a solid oral formulation, by a liquid formulation, including one applied as drops sub-lingually; by a tablet, lozenge, or lollipop held in the mouth and absorbed buccally or sublingually; by means of a suppository formulation administered rectally; or by a powder, gel, or suspension, or an intra-nasal spray formulation. The drug may also be administered in a sterile parenteral formulation by sub-cutaneous or intramuscular route, although sub-lingual, buccal, intra-nasal, and suppository formulations are preferred because of their greater ease of administration and the resulting greater potential for patient acceptance.

Sublingual apomorphine dosage forms, usually containing about 2.5 to about 10 milligrams of apomorphine, are useful in treating the symptoms of male vasculogenic sexual dysfunction, including its symptomatic manifestations without nausea or other undesirable side effects. The apomorphine is administered in the time period immediately prior to sexual intercourse, generally during the period between about 2 minutes and 120 minutes prior to sexual relations, preferably during the period between about 2 minutes and about 60 minutes prior to sexual relations so as to maintain a predetermined circulating serum levels and mid-brain tissue levels of apomorphine during the period of sexual activity sufficient to induce and maintain penile erection adequate for intercourse (i.e. "effective vasocongestive arousal") but less than the amount that induces nausea. Plasma concentrations of apomorphine are preferably maintained at between about 0.3 to 5.5 nanograms per milliliter, preferably between about 0.3 to about 4 nanograms per milliliter, and more preferably between about 1 to about 2 nanograms per milliliter. Apomorphine is a dopamine receptor agonist that has a recognized use as an emetic when administered subcutaneously in about a 5-milligram dose. For the purposes of the present invention, apomorphine is administered in an amount sufficient to excite cells in the mid-brain region of the patient but with minimal side effects. This cell excitation is believed to be part of a cascade of stimulation that is likely to include neurotransmission with serotonin and oxytocin.

The dopamine receptors in the mid-brain region of a patient can be stimulated to a degree sufficient to cause an erectile response without inducing nausea by the administration, preferably sublingually, of apomorphine so as to maintain a plasma concentration of apomorphine of no more than about 5.5 nanograms per milliliter (5.5 ng/ml). The sublingual administration usually takes place over a time period in the range of about 2 to about 10 minutes, or longer. The amount of apomorphine administered sublingually over this time period preferably is in the range of about 25 micrograms per kilogram ($\mu$g/kg) of body weight to about 60 $\mu$g/kg of body weight.

In sensitive patients experiencing nausea, the onset of nausea can be obviated or delayed by delivering apomorphine at a controlled dissolution rate so as to provide circulating serum levels and midbrain tissue levels of apomorphine less than 5.5 nanograms/mL. When apomorphine is administered at or near the higher amounts of the aforementioned dosage range, the likelihood of the onset of nausea can be reduced by concurrent administration of a ganglionic agent (inhibitor of ganglionic response) such as nicotine or lobeline sulfate. For this purpose, the weight ratio of apomorphine to ganglionic agent is in the range of about 10 to about 1.

Other antiemetic agents that can be used in conjunction with apomorphine are antidopaminergic agents such as metoclopramide, and the phenothiazines, e.g., chlorpromazine, prochlorperazine, pipamazine, thiethylperazine, oxypendyl hydrochloride, and the like. Also suitable are the serotonin (5-hydroxytryptamine or 5-HT) antagonists such as domperidone, ondansetron (commercially available as the hydrochloride salt under the designation Zofran™), and the like, the histamine antagonists such as buclizine hydrochloride, cyclizine hydrochloride, dimenhydrinate (Dramamine™), and the like, the parasympathefic depressants such as scopolamine, and the like, as well as other anti-emetics such as metopimazine, trimethobenzamide, benzauinamine hydrochloride, diphenidol hydrochloride, and the like.

Illustrative preferred sublingual dosage forms are set forth in Table I, below.

TABLE I

150-Milligram Apomorphine Hydrochloride Sublingual Tablets

| 3-mg Tablet | |
|---|---|
| Apomorphine Hydrochloride | 2.00 wt % |
| Mannitol | 66.67 wt % |
| Ascorbic Acid | 3.33 wt % |
| Citric Acid | 2.00 wt % |
| Avicel PH 102 | 15.00 wt % |
| Methocel E4 | 10.00 wt % |
| Aspartame | 0.67 wt % |
| Magnesium stearate | 0.33 wt % |
| 4-mg Tablet | |
| Apomorphine Hydrochloride | 2.66 wt % |
| Mannitol | 66.00 wt % |
| Ascorbic Acid | 3.33 wt % |
| Citric Acid | 2.00 wt % |
| Avicel PH102 | 15.00 wt % |
| Methocel E4M | 10.00 wt % |
| Aspartame | 0.67 wt % |
| Magnesium stearate | 0.33 wt % |
| 5-mg Tablet | |
| Apomorphine Hydrochloride | 3.33 wt % |
| Mannitol | 65.34 wt % |
| Ascorbic Acid | 3.33 wt % |
| Citric Acid | 2.00 wt % |
| Avicel PH102 | 15.00 wt % |
| Methocel E4M | 10.00 wt % |
| Aspartame | 0.67 wt % |
| Magnesium stearate | 0.33 wt % |

If desired, and in order to facilitate absorption and thus bioavailability, the presently contemplated dosage forms can also contain, in addition to tabletting excipients, $\beta$-cyclodextrin or a $\beta$-cyclodextrin derivative such as hydroxypropyl-$\beta$-cyclodextrin (HPBCD). Illustrative dosage forms containing HPBCD are shown in Tables II and III, below.

TABLE II

Apomorphine Hydrochloride Sublingual Tablets With Hydroxypropyl-$\beta$-Cyclodextrin

| Ingredient | mg/Tab |
|---|---|
| Apomorphine hydrochloride | 4.0 |
| HPBCD | 5.0 |
| Ascorbic acid | 10.0 |
| PEG 8000 | 39.5 |
| Mannitol | 39.5 |
| Aspartame | 2.0 |
| Total | 100.0 |

TABLE III

Apomorphine Hydrochloride Sublingual Tablets With β-Cyclodextrin

| Ingredient | mg/Tab |
|---|---|
| Apomorphine hydrochloride | 5.0 |
| β-Cyclodextrin | 20.0 |
| Ascorbic acid | 5.0 |
| Mannitol | 68.9 |
| Magnesium stearate | 1.0 |
| D&C Yellow 10 aluminum lake | 0.1 |
| TOTAL | 100.0 |

Nicotine- and domperidone-containing dosage forms are illustrated in Table IV, below.

TABLE IV

Apomorphine Hydrochloride Sublingual Tablets Containing an Anti-Emetic Agent

| Ingredient | mg/Tab |
|---|---|
| Nicotine-containing tablet | |
| Apomorphine Hydrochloride | 5.0 |
| Ascorbic Acid | 5.0 |
| Mannitol | 67.9 |
| Magnesium Stearate | 1.0 |
| Nicotine | 1.0 |
| β-Cyclodextrin | 20.0 |
| D&C Yellow aluminum lake | 0.1 |
| TOTAL | 100.0 |
| Domperidone-containing tablet | |
| Apomorphine Hydrochloride | 5.0 |
| Ascorbic Acid | 5.0 |
| Mannitol | 58.9 |
| Magnesium Stearate | 1.0 |
| Domperidone | 10.0 |
| β-Cyclodextrin | 20.0 |
| D&C Yellow 10 aluminum lake | 0.1 |
| TOTAL | 100.0 |

The preferred sublingual dosage forms dissolve within a time period of less than about 10 minutes. The dissolution time can be essentially instantaneous or, if desired, as long as the necessary plasma concentration of apomorphine is to be maintained. Preferably, the dissolution time in water for the presently contemplated dosage forms is about 3 minutes to about 5 minutes.

A multi-center, double-blind, randomized, placebo-controlled, three-armed study was conducted on patients diagnosed with male erectile dysfunction. For each sequence, patients received placebo in one of the treatment periods, and a dose (2 mg, 4 mg, 5 mg, or 6 mg) of apomorphine in the other treatment period. This arrangement resulted in approximately one-third of the patients receiving one of the three apomorphine doses.

During treatment periods of the study, patients and their sexual partners were instructed to attempt intercourse a minimum of twice weekly. Each time the study drug was taken, a questionnaire was completed by the patient and mailed to the study sponsor. The questionnaire recorded the date and time the study drug was taken, an evaluation of the erection, whether or not sexual intercourse had occurred, and satisfaction associated with each attempt. The patient also completed a diary which recorded the latency and duration of erections associated with the use of the study drug and anti-emetic and concomitant medication usage and any adverse effects. If an erection occurred after administration to the patient of the study drug, the duration of erection and time-to-erection were recorded in the patient diary. The data from these studies were analyzed, and the results from patients who were diagnosed as hypertensive, or who were taking a hypertensive medication, were tabulated. These study results appear in Tables V–VII below.

Table V shows the responses on the questionnaire question, "Did you achieve an erection firm enough for intercourse?" of study participants receiving placebo or one of four doses (2 mg, 4, mg, 5 mg, or 6 mg) of apomorphine.

TABLE V

Erection Firm Enough for Intercourse (Based on Attempts*)

| Dose | No. of Patients | Response | Apomorphine Attempts (Percent) | | Placebo Attempts (Percent) | | P-Value |
|---|---|---|---|---|---|---|---|
| 2 mg | 65 | Yes | 210 | 43.30 | 162 | 34.11 | 0.028 |
| 2 mg | | No | 275 | 56.70 | 309 | 65.61 | |
| 4 mg | 53 | Yes | 202 | 52.60 | 105 | 27.06 | <0.001 |
| 4 mg | | No | 182 | 47.40 | 283 | 72.94 | |
| 5 mg | 26 | Yes | 95 | 49.48 | 62 | 30.85 | 0.022 |
| 5 mg | | No | 97 | 50.52 | 139 | 69.15 | |
| 6 mg | 50 | Yes | 233 | 62.13 | 119 | 32.96 | <0.001 |
| 6 mg | | No | 142 | 37.87 | 242 | 67.04 | |

*An "attempt" was defined as the taking of study drug and completion of the appropriate questionnaire efficacy question.

The data in Table V show that apomorphine, at each dose tested, significantly increased the percentage of reported erections which were firm enough for intercourse. While not holding to one theory to the exclusion of others, it is believed that the slightly lower "yes" responses for the 5 mg dose when compared with the 4 mg dose reflects the smaller patient population for the 5 mg dose study.

Table VI shows the "success" responses on the questionnaire from study participants receiving placebo or one of four doses (2 mg, 4, mg, 5 mg, or 6 mg) of apomorphine. A treatment was deemed a "success" for a patient if at least 50% of the first eight attempts while using the treatment resulted in erections firm enough for intercourse. Table VI shows the percentages of patients classified as treatment success. The results show success rates of 68.0% for drug vs. 38.8% for placebo at the 6 mg drug dose; 53.8% for drug vs. 38.5% for placebo at the 5 mg drug dose; 62.3% for drug vs.

TABLE VI

"Successful" Erections Firm Enough for Intercourse

| | Placebo | | |
|---|---|---|---|
| | Successful | Not Successful | Total |
| Apomorphine 2 mg | | | |
| Successful | 21 (32.3%) | 8 (12.3%) | 29 (44.6%) |
| Not Successful | 4 (6.2%) | 32 (49.2%) | 36 (55.4%) |
| Total | 25 (38.5%) | 40 (61.5%) | 65 (100%) |
| Apomorphine 4 mg | | | |
| Successful | 12 (22.6%) | 21 (39.6%) | 33 (62.3%) |
| Not Successful | 3 (5.7%) | 17 (32.1%) | 20 (37.7%) |
| Total | 15 (28.3%) | 38 (71.7%) | 53 (100%) |

TABLE VI-continued

"Successful" Erections Firm Enough for Intercourse

|  | Placebo | | |
| --- | --- | --- | --- |
|  | Successful | Not Successful | Total |
| Apomorphine 5 mg | | | |
| Successful | 8 (30.8%) | 6 (23.1%) | 14 (53.8%) |
| Not Successful | 2 (7.7%) | 10 (38.5%) | 12 (46.2%) |
| Total | 10 (38.5%) | 16 (61.5%) | 26 (100%) |
| Apomorphine 6 mg | | | |
| Successful | 18 (36.0%) | 16 (32.0%) | 34 (68.0%) |
| Not Successful | 1 (2.0%) | 15 (30.0%) | 16 (32.0%) |
| Total | 19 (38.0%) | 31 (62.0%) | 50 (100%) |

26.9% for placebo at the 4 mg drug dose; and 44.6% for drug vs. 38.5% for placebo at the 2 mg drug dose. The results were statistically significant for the 4 mg and 6 mg doses; while showing a favorable success rate for the 2 mg and 5 mg doses, the lack of statistical significance is possibly due to the small sample size.

Finally, Table VII shows the results of the number of attempts which actually resulted in intercourse as reported by study participants on the questionnaire.

TABLE VII

Attempt Resulted in Intercourse (Based on First Eight Attempts*)

| Dose | No. of Patients | Response | Apomorphine Attempts (Percent) | | Placebo Attempts (Percent) | | P-Value |
| --- | --- | --- | --- | --- | --- | --- | --- |
| 2 mg | 65 | Yes | 185 | 38.22 | 148 | 31.36 | 0.080 |
| 2 mg |  | No | 299 | 61.78 | 324 | 68.64 |  |
| 4 mg | 52 | Yes | 183 | 47.66 | 87 | 22.96 | <0.001 |
| 4 mg |  | No | 201 | 52.34 | 292 | 77.04 |  |
| 5 mg | 26 | Yes | 100 | 52.08 | 62 | 30.85 | 0.012 |
| 5 mg |  | No | 92 | 47.92 | 140 | 69.65 |  |
| 6 mg | 50 | Yes | 205 | 56.01 | 96 | 26.67 | <0.001 |
| 6 mg |  | No | 161 | 43.99 | 264 | 73.33 |  |

*An "attempt" was defined as the taking of study drug and completiom of the appropriate questionnaire efficacy question.

The results presented in Table VII parallel those of Table V, with the percentage of attempts which resulted in intercourse being 56.01% for drug vs. 26.67% for placebo at the 6 mg drug dose; 52.08% for drug vs. 30.35% for placebo at the 5 mg drug dose; 47.66% for drug vs. 22.96% for placebo at the 4 mg drug dose; and 38.22% for drug vs. 31.36% for placebo at the 2 mg drug dose.

The data presented in Tables V–VII demonstrate that the administration of apomorphine to males suffering hypertension, a representative vasculogenic cause for erectile dysfunction, is successful in treating or ameliorating the condition.

While there have been shown and described what are believed to be the preferred embodiments of the present invention, it will be clear to one of ordinary skill in the art that various modifications can be made in the practice of the invention without departing from its scope as defined by the appended claims.

What is claimed is:

1. A method of treating male organic erectile dysfunction having a vasculogenic origin comprising orally administering to a male in need of such treatment a therapeutically effective amount of apomorphine or a pharmaceutically acceptable salt thereof.

2. The method of claim 1 wherein said organic erectile dysfunction having a vasculogenic origin relates to a disease of the cardiovascular system.

3. The method of claim 1 wherein said organic erectile dysfunction having a vasculogenic origin relates to a risk factor associated with a disease of the cardiovascular system selected from the group consisting of cigarette smoking, diabetes mellitus, vascular disease and arthritis.

4. The method of claim 2 wherein said disease of the cardiovascular system is selected from the group consisting of myocardial infarction, heart disease, and peripheral vascular disease.

5. The method of claim 2 wherein said disease of the cardiovascular system is impaired circulation associated with diabetes, cardiac bypass surgery, cerebral vascular trauma, or cigarette smoking.

6. The method of claim 1 wherein said apomorphine is administered in an amount sufficient to produce an effective penile erection in said male, but insufficient to induce nausea.

7. The method of claim 1 wherein said apomorphine is co-administered with an emesis inhibitory effective amount of an anti-emetic agent.

8. The method of claim 1 wherein said apomorphine is administered in an amount between about 25 micrograms/kg of body weight and about 60 micrograms/kg of body weight.

9. The method of claim 1 wherein said apomorphine is administered in an amount sufficient to establish plasma concentration levels of apomorphine ranging between about 0.3 to about 5.5 nanograms/mL.

10. The method of claim 9 wherein said plasma levels of apomorphine range between about 0.3 and about 4 nanograms/mL.

11. The method of claim 10 wherein said plasma levels of apomorphine range between about 1 and about 2 nanograms/mL.

12. The method of claim 7 wherein said anti-emetic agent is selected from the group consisting of nicotine, lobeline sulfate, metoclopramide, chlorpromazine, prochlorperazine, pipamazine, thiethylperazine, oxypendyl hydrochloride, domperidone, ondansetron, buclizine hydrochloride, cyclizine hydrochloride, dimenhydrinate, scopolamine, metopimazine, trimethobenzamide, benzauinamine hydrochloride, and diphenidol hydrochloride.

13. A method of treating erectile dysfunction in a hypertensive male comprising orally administering to a male in need of such treatment a therapeutically effective amount of apomorphine or a pharmaceutically acceptable salt thereof.

14. The method of claim 13 wherein said apomorphine is co-administered with an emesis inhibitory effective amount of an anti-emetic agent.

15. The method of claim 13 wherein said apomorphine is administered in an amount between about 25 micrograms/kg of body weight and about 60 micrograms/kg of body weight.

16. The method of claim 13 wherein said apomorphine is administered in an amount sufficient to establish plasma concentration levels of apomorphine ranging between about 0.3 to about 5.5 nanograms/mL.

17. The method of claim 16 wherein said plasma levels of apomorphine range between about 0.3 and about 4 nanograms/mL.

18. The method of claim 17 wherein said plasma levels of apomorphine range between about 1 and about 2 nanograms/mL.

19. The method of claim 14 wherein said anti-emetic agent is selected from the group consisting of nicotine, lobeline sulfate, metoclopramide, chlorpromazine, prochlorperazine, pipamazine, thiethylperazine, oxypendyl hydrochloride, domperidone, ondansetron, buclizine hydrochloride, cyclizine hydrochloride, dimenhydrinate, scopolamine, metopimazine, trimethobenzamide, benzauinamine hydrochloride, and diphenidol hydrochloride.

20. A method of treating male organic erectile dysfunction having a vasculogenic origin comprising orally administering to a male in need of such treatment a therapeutically effective amount of a pharmaceutically acceptable ester of apomorphine, wherein said ester is selected from the group consisting of alkanoic esters, alkenoic esters, cycloalkanoic esters and alkanedioic esters.

21. A method of treating erectile dysfunction in a hypertensive male comprising orally administering to a male in need of such treatment a therapeutically effective amount of a pharmaceutically acceptable ester of apomorphine, wherein said ester is selected from the group consisting of alkanoic esters, alkenoic esters, cycloalkanoic esters and alkanedioic esters.

* * * * *

UNITED STATES PATENT AND TRADEMARK OFFICE
CERTIFICATE OF CORRECTION

PATENT NO.    : 6,291,471 B1
DATED         : September 18, 2001
INVENTOR(S)   : Karen Kling et al.

It is certified that error appears in the above-identified patent and that said Letters Patent is hereby corrected as shown below:

Title page,
Item [73] Assignee, replace "ABB Holdings, Inc.," with -- TAP Holdings, Inc., --.

Column 9,
Line 63, replace "male organic erectile dysfunction" with -- non-psychogenic male organic erectile dysfunction --.

Column 10,
Line 45, replace "treating erectile dysfunction in a" with -- treating non-psychogenic erectile dysfunction in a --.

Column 11,
Line 6, replace "treating male organic erectile" with -- treating non-psychogenic male organic erectile --.

Column 3,
Line 3, replace "treating erectile dysfunction in a hypertensive" with -- treating non-psychogenic erectile dysfunction in a hypertensive --.

Signed and Sealed this

Fourth Day of June, 2002

Attest:

Attesting Officer

JAMES E. ROGAN
*Director of the United States Patent and Trademark Office*